(12) United States Patent    (10) Patent No.:    US 6,648,819 B2
Lee                          (45) Date of Patent:    Nov. 18, 2003

(54) PUPIL DILATOR

(76) Inventor: Yau Wing Lee, 1D, Block 7, Meadowlands, Yuen Long, New Territories, HKSAR (CN)

( * ) Notice: Subject to any disclaimer, the term of this patent is extended or adjusted under 35 U.S.C. 154(b) by 15 days.

(21) Appl. No.: 09/987,700

(22) Filed: Nov. 15, 2001

(65) Prior Publication Data

US 2003/0092970 A1 May 15, 2003

(51) Int. Cl.$^7$ ................................................ A61B 17/02
(52) U.S. Cl. ........................ 600/236; 600/208; 606/107
(58) Field of Search ................................ 600/236, 206, 600/208; 606/107

(56) References Cited

U.S. PATENT DOCUMENTS

| 4,387,706 A | * | 6/1983 | Glass |
| 4,782,820 A |   | 11/1988 | Woods |
| 4,991,567 A | * | 2/1991 | McCuen, II et al. ........ 606/107 |
| 5,163,419 A |   | 11/1992 | Goldman |
| 5,267,553 A |   | 12/1993 | Graether |
| 5,322,054 A |   | 6/1994 | Graether |
| 5,374,272 A | * | 12/1994 | Arpa et al. .................. 600/107 |
| 5,607,446 A | * | 3/1997 | Beehler et al. .............. 600/198 |
| 5,634,884 A |   | 6/1997 | Graether ...................... 600/236 |

FOREIGN PATENT DOCUMENTS

WO    WO 96/29965    * 10/1996

* cited by examiner

*Primary Examiner*—Cary E. O'Connor
(74) *Attorney, Agent, or Firm*—Jacobson Holman PLLC

(57) ABSTRACT

A pupil dilator including a discontinuous resilient ring adapted to be temporarily straightened by an applicator for insertion into, or removal from, the anterior chamber of an eye. The applicator includes an elongate tube with first and second ends. The first end of the tube is open. A retractor is slidably disposed within the tube and is movable from a first position to a second position. The retractor has a grasper at one end that is adapted to engage the pupil dilator when the retractor is in the first position. When the retractor is moved to the second position the pupil dilator is drawn into the tube, at the same time straightening it.

9 Claims, 4 Drawing Sheets

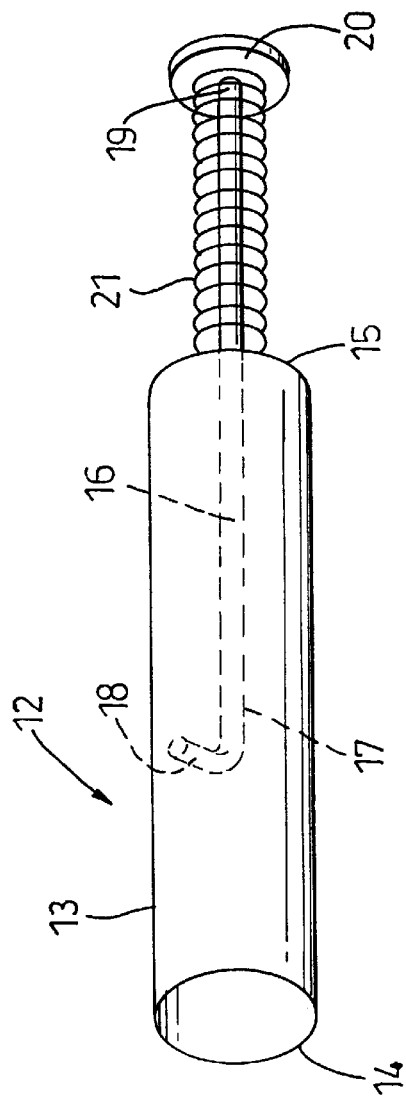
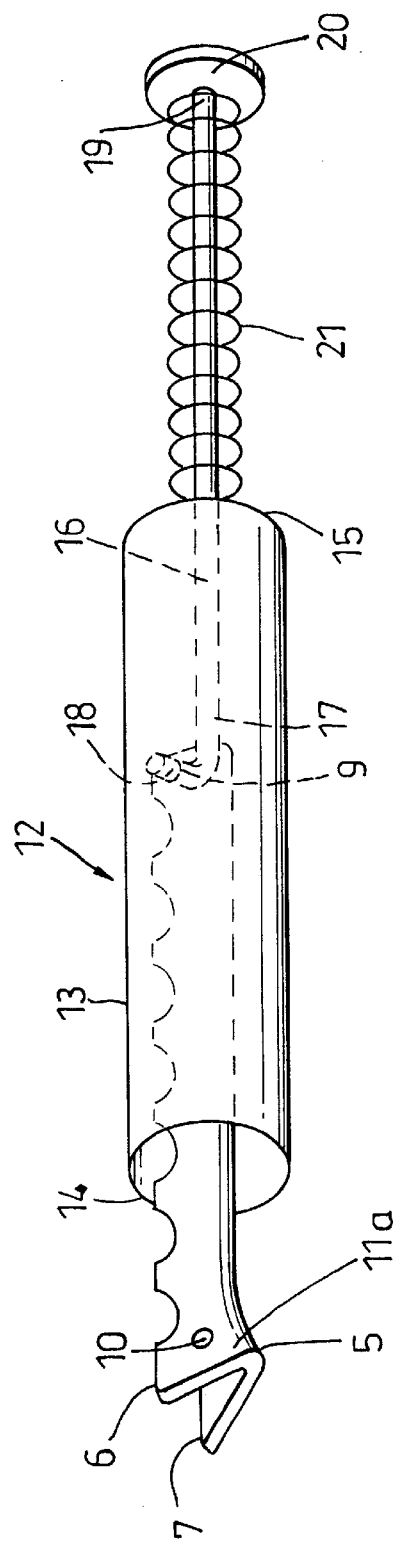
Fig. 6
Fig. 7

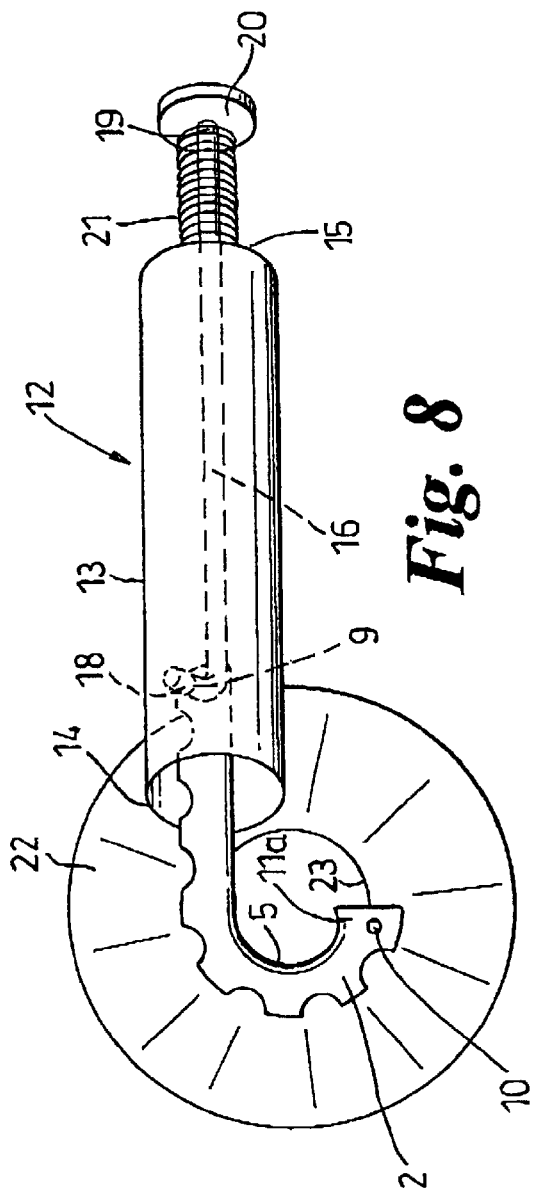
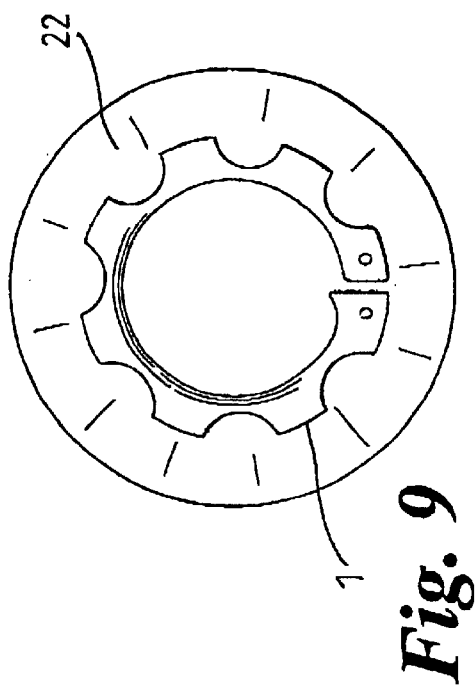
Fig. 8
Fig. 9

PUPIL DILATOR

FIELD OF THE INVENTION

The invention relates to mechanical pupil dilators and to applicators for mechanical pupil dilators.

BACKGROUND TO THE INVENTION

Light reaches the retina of the eye through the pupillary opening (the pupil) in the iris. A normal pupil is capable of reacting to light by constriction and reacting to dark by dilation in order to control the amount of light reaching the retina. In a diseased iris, such as the iris of a patient with diabetic mellitus, uveitis or chronic use of miotic eye drops, the pupillary opening remains small all of the time.

Cataract is one of the leading causes of blindness in the world. In the developed world the incidence of diabetes is increasing. Diabetic patients are well known for having small pupils. Additionally, diabetics have a higher incidence of cataract, vitreous haemorrhage and retinal detachment than the general population.

Small pupil patients pose a major problem and challenge in ophthalmic surgery. When such small pupil patients have cataract or vitreo-retinal surgery and pupil cannot be easily dilated by mydraiatic eye drops. Surgery is very difficult unless the pupil can be mechanically dilated.

SUMMARY OF THE INVENTION

It is an object of the present invention to provide a mechanical pupil dilator for use in eye surgery. It is a further object of the present invention to provide an apparatus for inserting and removing said pupil dilator.

According to a first aspect of the invention there is provided a pupil dilator comprising a discontinuous resilient ring adapted to be temporarily straightened linearly for insertion into, or removal from, the anterior chamber of the eye. The discontinuous resilient ring has first and second ends proximate each other and a periphery adapted to engage the periphery of the pupillary opening in the iris of an eye, at least the first end of the resilient ring is adapted to be engaged by a pupil dilator applicator tool.

Preferably, the resilient ring is substantially V shaped in cross-section, the vertex of the V is orientated radially inwards towards the center of the ring and the inner portion of the V provides an outwardly orientated groove adapted to engage the periphery of the pupillary opening in the iris.

The first end of the resilient ring has an aperture in it adapted for engagement by an applicator. The pupil dilator is inserted into the anterior chamber of the eye through a single corneal opening with the aid of the applicator. The ring is adapted to enlarge and stretch the pupillary opening in the iris, hence enlarging the pupil.

To aid engagement, the second end of the resilient ring is adapted to slide along the periphery of the pupillary opening by being curved radially inwards.

According to a second aspect of the invention there is provided a pupil dilator applicator including an elongate tube having first and second ends with at least the first end being open, and a retractor slidably disposed within the tube and being movable from a first position to a second position, the retractor having an grasper at one end thereof, the grasper adapted to engage a pupil dilator when the retractor is in the first position. Moving the retractor to the second position draws the pupil dilator into the tube.

The retractor is an elongate rod slidably disposed within the second end of the tube, the rod bearing the grasper at its first end within the tube and a handle at its second end external to the tube, the handle facilitates movement of the retractor between the first and second positions.

The grasper is a hook adapted to engage with the aperture in the first end of the resident ring.

The retractor is biased in the second position by a spring.

According to a third aspect of the invention there is provided a method of dilating a pupil including:

a pupil dilator comprising a discontinuous resilient ring adapted to be temporarily straightened by an applicator for insertion into, or removal from, the anterior chamber of the eye;

an applicator comprising an elongate tube having first and second ends with at least the first end open, and a retractor slidably disposed within the tube and being movable from a first position to a second position, the retractor having an grasper at one end, the grasper adapted to engage the pupil dilator when the retractor is in the first position, and wherein when the retractor is moved to the second position the pupil dilator is drawn into the tube; wherein a first end of the discontinuous resilient ring is grasped with the grasper and the retractor moved to the second position to draw the resilient ring into the applicator tube, at the same time straightening the resilient ring, inserting the applicator tube into the anterior chamber of an eye through an incision in the cornea or sclera, moving the retractor from the second position to the first position so as to eject the pupil dilator from the applicator tube, and at the same time positioning the applicator tube so as to guide the ejected pupil dilator onto the periphery of the pupillary opening.

The method is performed prior to lens or vitreo-retinal surgery to enlarge the pupil.

The pupil dilator is removed in the reverse sequence by grasping one end of the resilient ring with the grasper and drawing the ring into the applicator tube, and withdrawing the applicator tube from the anterior chamber of the eye.

Further aspects of the invention will become apparent from the following description, which is given by way of example only.

BRIEF DESCRIPTION OF THE DRAWINGS

Embodiments of the invention will now be described by way of example only and with reference to the accompanying drawings in which:

FIG. 6 illustrates a pupil dilator applicator according to the invention, FIG. 7 illustrates the applicator engaged with a pupil dilator, FIG. 8 illustrates the pupil dilator being inserted onto the pupillary opening of an eye, and FIG. 9 illustrates the pupil dilator in place in the iris.

DESCRIPTION OF THE PREFERRED EMBODIMENTS

For fullness, dimensions of the preferred embodiment are given in the following description, however these are not critical to the invention and are not to be construed as being limiting on the appended claims.

Figure 5:
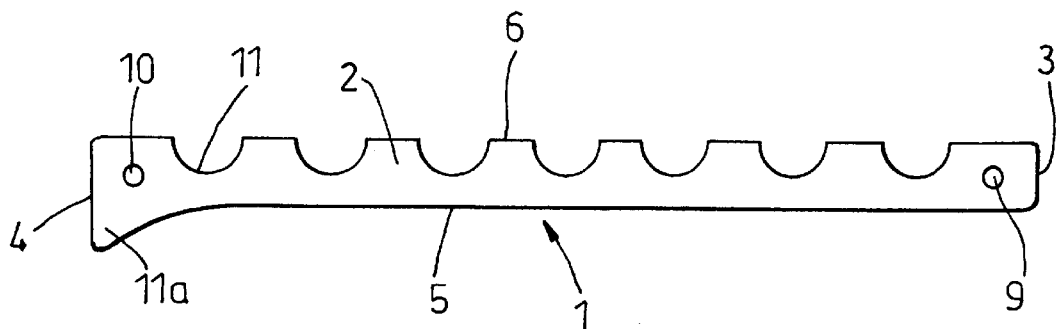
FIG. 5 illustrates a view of the pupil dilator temporarily straightened.

Referring to FIGS. 1 to 5, a pupil dilator 1 comprises a discontinuous resilient ring 2 having its first end 3 and its second end 4 proximate each other. The resilient ring 2 is capable of being temporarily straightened in a substantially linear way as shown in FIG. 5.

Figure 1:
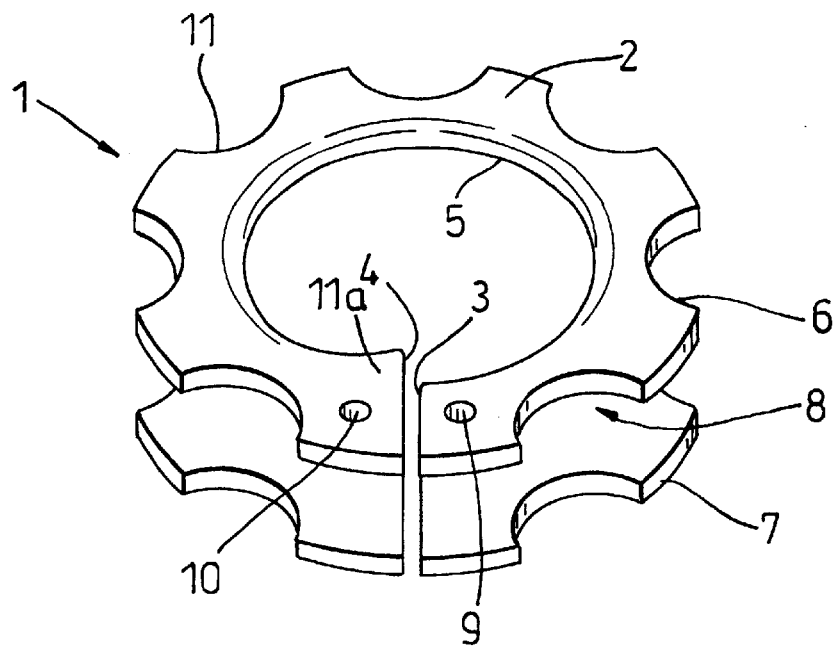
FIG. 1 illustrates a perspective view of a pupil dilator according to the invention.
Figure 2:
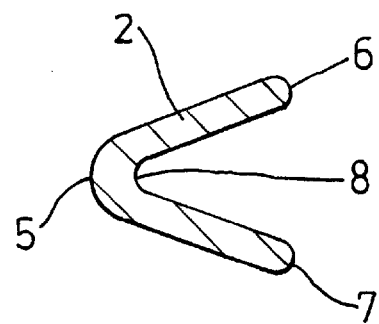
FIG. 2 illustrates a cross-section through the pupil dilator.
Figure 3:
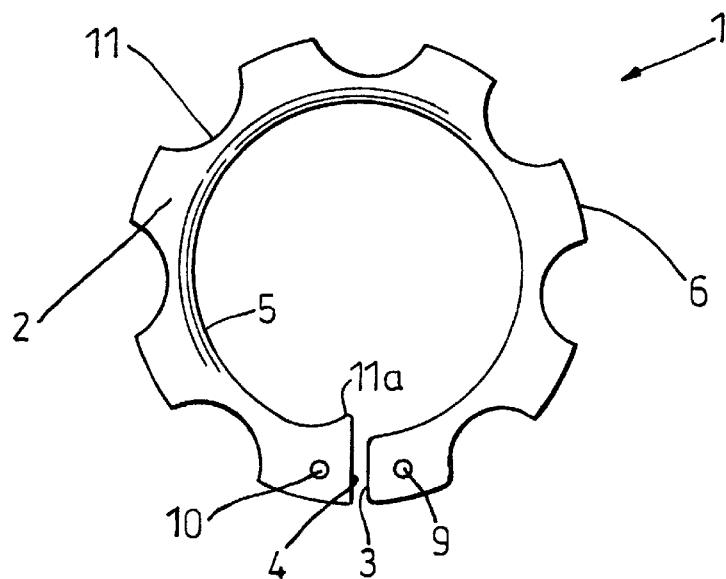
FIG. 3 illustrates a plan view of the pupil dilator.
Figure 4:
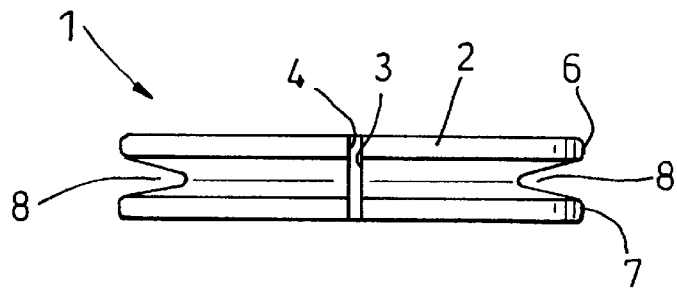
FIG. 4 illustrates a side view of the pupil dilator.

The resilient ring 2 is substantially V shaped in cross-section as shown in FIG. 2. The vertex 5 of the V is orientated radially inwards towards the centre of the ring. The side members 6, 7 of the V extend radially outwards and the inner portion of the V forms a groove 8 around the outer periphery of the resilient ring 2 which is adapted to engage the periphery of the pupillary opening in the iris of an eye.

To facilitate the temporary straightening of the resilient ring 2 the outer periphery of the side members 6, 7 have scalloped portions 11 provided therein. The purpose and benefit of the scalloped portions 11 will be apparent to the skilled addressee.

The first end 3 of the resilient ring 2 has an aperture 9 so as to be adapted for engagement by an applicator tool. In an alternative embodiment, the second end 4 of the resilient ring 2 has a second aperture 10 so as to be adapted for engagement by the applicator tool.

The periphery at second end 4 of resilient ring 2 is curved inwardly to form a lip portion 11a. It will become apparent later in this description that the inwardly curved lip portion 11a allows the resilient ring 2 to be easily and safely guided onto the periphery of the pupillary opening.

In the preferred embodiment the resilient ring 2 has an internal diameter of 6.5 mm, thus it is able to dilate the pupillary opening to 6.5 mm. The width of the resilient ring 2 (the distance between vertex 5 and outer peripheries 6, 7) is 1.5 mm, and the thickness of the resilient ring 2 (distance between the peripheries of side members 6, 7) is 1 mm.

Referring to FIG. 6, there shown is a pupil dilator applicator tool 12. The applicator 12 comprises an elongate hollow tube 13 having a first end 14 and a second end 15. End 14 is open to allow access to the interior of the tube 13. In the preferred embodiment the external diameter of the tube 13 is 2.5 mm allowing it to be inserted through a 3 mm standard corneal tunnel created intra-operatively for Phacoemulsification.

Slidably disposed within second end 15, and axially with the tube 13, is an elongate retractor rod 16. The first end 17 of the retractor 16 is located within tube 13 and is bent to form a grasper hook 18. At the second end 19 of retractor 16 is a handle 20. The handle 20 facilitates movement of the retractor 16 between a first position (not shown) wherein the hook 18 extends beyond the opening in the first end 14 of tube 13, and a second position (not shown) wherein the hook 18 is located within the tube 13 near second end 15. A spring 21 located about retractor rod 16, and between handle 20 and tube end 15, biases the retractor 16 in the second position.

FIGS. 7 and 8 illustrate how the applicator 12 is used in conjunction with a pupil dilator 1. Firstly, the pupil dilator 1 is loaded into the applicator 12. To do this the handle 20 is depressed to move the retractor rod 16 to the first position wherein the hook 18 extends beyond opening 14 in tube 13. Hook 18 is engaged with aperture 9 in first end 3 of resilient ring 2. Handle 20 is released slowly to allow retractor 16 to return to the second position at the same time drawing the resilient ring 2 into tube 13. As resilient ring 2 is drawn into tube 13 it is temporarily straightened as illustrated in FIG. 7. When the retractor 16 is in the second position the temporarily straightened resilient ring 2 is fully located within tube 13.

With the pupil dilator 1 loaded into the applicator 12 the applicator tube 13 can inserted through an opening created in the cornea or sciera of the eye.

Referring to FIG. 8, with the applicator tube 13 in the anterior chamber of the eye the handle 20 is depressed again to eject/unload the pupil dilator 1. As the handle 20 is depressed the retractor 16 moves from the second position to the first position and the resilient ring 2 is ejected from tube 13, second end 4 first. The applicator tube 13 is positioned so that the curved lip 11 of the resilient ring 2 engages the periphery 23 of the pupillary opening in the iris 22 of the eye. As the resilient ring 2 is slowly ejected it returns to its circular "ring" shape. The resilient ring 2 is gradually guided onto the periphery 23 of the pupillary opening until it is fully ejected from the applicator tube 13. It is then in place on the periphery 23 of the pupillary opening and the pupil is mechanically dilated. The hook 18 is detached from the aperture 9 and the applicator tube 13 is removed from within the anterior chamber. FIG. 9 illustrates the pupil dilator 1 in place on the iris 22 of the eye. Lens or vitreo-retinal surgery can now take place.

After lens or vitreo-retinal surgery the applicator tube 13 is again inserted through the opening in the cornea into the anterior chamber of the eye. The handle 20 is depressed to extend the hook 18 beyond the open end 14 of tube 13. The hook 18 is engaged with either aperture 9 of first end 3 or aperture 10 of second end 4 of resilient ring 2. The handle 20 is released slowly moving the retractor 16 to the second position so that resilient ring 2 is drawn into the tube 13, straightening it and removing it from the periphery 23 of the pupillary opening. When the resilient ring 2 is fully within the tube 13 it can be removed from the anterior chamber. The pupil can return to its unstretched normal size.

Thus, the invention provides a mechanical pupil dilator and an applicator that can be inserted though a single small opening in the cornea of the eye, are quick and easy to insert and remove and are safe.

Where in the foregoing description reference has been made to integers or elements have known equivalents then such are included as if individually set forth herein.

Embodiments of the invention have been described, however it is understood that variations, improvement or modifications can take place without departure from the sprite of the invention or scope of the appended claims.

I claim:

1. A pupil dilator comprising
a discontinuous resilient ring having first and second ends proximate each other and a periphery for engaging a periphery of a pupillary opening in an iris of an eye, the resilient ring adapted to be temporarily straightened linearly to facilitate insertion into, or removal from, an anterior chamber of the eye, and at least the first end of the resilient ring having an aperture for engagement by an applicator, and the second end of the resilient ring having a lip for sliding along the periphery of the pupillary opening.

2. The pupil dilator as claimed in claim 1, wherein the resilient ring is substantially V shaped in cross-section, a vertex of the V is oriented radially inwards towards a center of the ring and an inner portion of the V provides an outwardly orientated groove adapted to engage the periphery of the pupillary opening in the iris.

3. The pupil dilator as claimed in claim 1, wherein the second end of the resilient ring is curved radially inwards.

4. The pupil dilator as claimed in claim 1, further comprising an applicator including an elongate tube having first and second ends with at least the first end open, and a retractor slidably disposed within the tube and being movable from a first position to a second position, the retractor having a hook for engaging the aperture when the retractor is in the first position.

5. The pupil dilator applicator as claimed in claim 4, wherein the retractor is an elongate rod slidably disposed within the second end of the tube, the rod having the hook at its first end within the tube and a handle at its second end external to the tube.

6. The pupil dilator applicator as claimed in claim 4, wherein the retractor is biased in the second position by a spring.

7. A method of dilating a pupil including:

a pupil dilator comprising a discontinuous resilient ring adapted to be temporarily straightened by an applicator for insertion, or removal from, beneath the cover (cornea) of the eye;

an applicator comprising an elongate tube having first and second ends with at least the first end open, and a retractor slidably disposed within the tube and being movable from a first position to a second position, the retractor having an grasper at one end, the grasper adapted to engage the pupil dilator when the retractor is in the first position; and wherein a first end of the discontinuous resilient ring is grasped with the grasper and the retractor moved to the second position to draw the resilient ring into the applicator tube, at the same time straightening the resilient ring, inserting the applicator tube into the anterior chamber of an eye through an incision in the cornea or sclera, moving the retractor from the second position to the first position so as to eject the pupil dilator from the applicator tube, and at the same time positioning the applicator tube so as to guide the ejected pupil dilator onto the periphery of the pupillary opening.

8. A method of dilating a pupil as claimed in claim 7 when performed prior to lens or vitreo-retinal surgery.

9. A method of dilating a pupil as claimed in claim 8 wherein the pupil dilator is removed by grasping one end of the resilient ring with the grasper and drawing the ring into the applicator tube, and withdrawing the applicator tube, with pupil dilator, from the anterior chamber of the eye.

* * * * *